US 6,602,244 B2

(12) United States Patent
Kavanagh et al.

(10) Patent No.: US 6,602,244 B2
(45) Date of Patent: Aug. 5, 2003

(54) LUBRICATING AND GRIPPING DEVICE FOR URINARY CATHETER PACKAGE

(75) Inventors: Seamus T. Kavanagh, County Mayo (IE); Martin P. Creaven, County Mayo (IE)

(73) Assignee: Hollister Incorporated, Libertyville, IL (US)

( * ) Notice: Subject to any disclaimer, the term of this patent is extended or adjusted under 35 U.S.C. 154(b) by 89 days.

(21) Appl. No.: 09/909,223

(22) Filed: Jul. 19, 2001

(65) Prior Publication Data

US 2003/0018302 A1 Jan. 23, 2003

(51) Int. Cl.[7] .................. A61M 27/00; A61M 5/00; A61M 25/00; A61M 31/00; A61M 1/00
(52) U.S. Cl. ................. 604/544; 604/172; 604/263; 604/265; 604/275; 604/327
(58) Field of Search ................. 604/540, 544, 604/171, 172, 257, 202, 203, 265, 275, 507, 250, 327

(56) References Cited

U.S. PATENT DOCUMENTS

| 3,556,294 A | 1/1971 | Walck, III ............... 206/63.2 |
| 3,854,483 A | 12/1974 | Powers |
| 3,898,993 A | * 8/1975 | Taniguchi ................. 604/172 |
| 3,934,721 A | 1/1976 | Juster et al. ................ 206/364 |
| 4,062,363 A | 12/1977 | Bonner, Jr. |
| 4,230,115 A | 10/1980 | Walz, Jr. et al. |
| 4,622,033 A | * 11/1986 | Taniguchi ................. 604/172 |
| 4,652,259 A | 3/1987 | O'Neil ........................ 604/54 |
| 5,147,341 A | 9/1992 | Starke et al. ............... 604/349 |
| 5,226,530 A | 7/1993 | Golden ....................... 206/210 |
| 5,454,798 A | 10/1995 | Kubalak et al. ............ 604/328 |
| 6,004,305 A | 12/1999 | Hursman et al. ........... 604/328 |
| 6,053,905 A | 4/2000 | Daignault, Jr. et al. ..... 604/544 |
| 6,090,075 A | * 7/2000 | House ......................... 604/172 |
| 2002/0103467 A1 | * 8/2002 | Kubalak ..................... 604/327 |

FOREIGN PATENT DOCUMENTS

| DE | 0 677 299 | 4/2001 |
| WO | 98/06642 | 2/1998 |

* cited by examiner

Primary Examiner—Karen Reichle
(74) Attorney, Agent, or Firm—Marshall, Gerstein & Borun

(57) ABSTRACT

A device for lubricating a urinary catheter and for normally and automatically gripping the catheter but selectively releasing such catheter only when squeezing forces are applied by a user's fingers during a catheterization procedure. Such a device is also combined with a protective container which preferably may also be used as a urine collecting pouch.

20 Claims, 2 Drawing Sheets

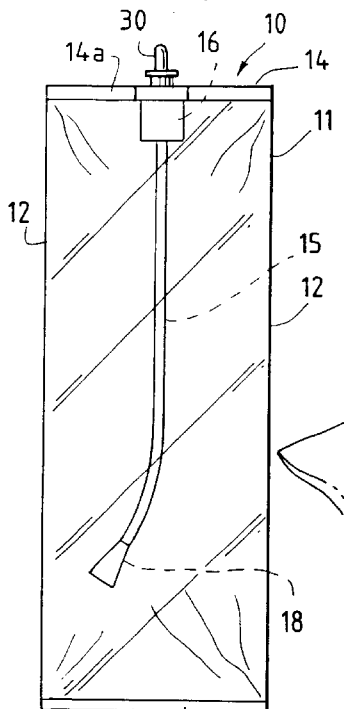
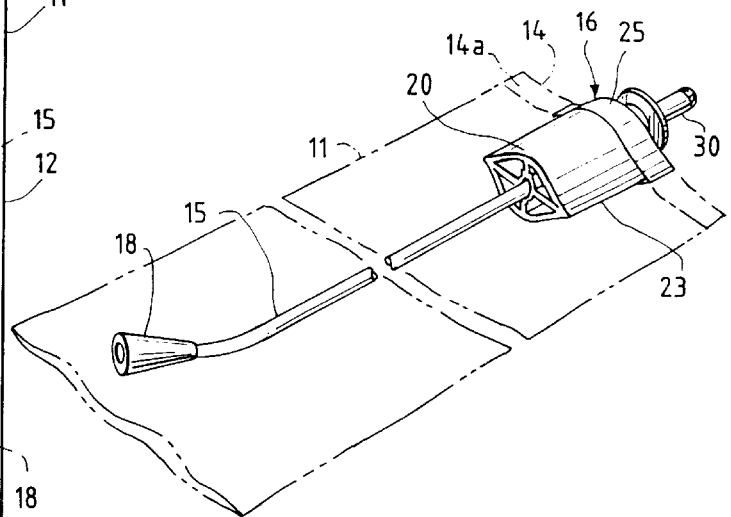
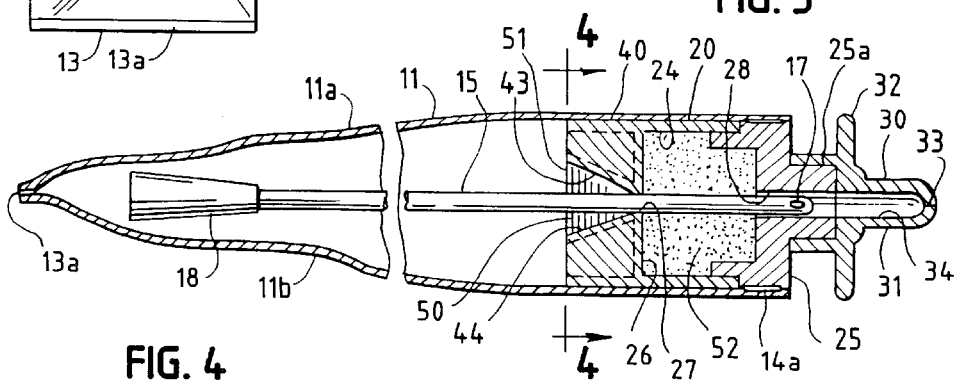
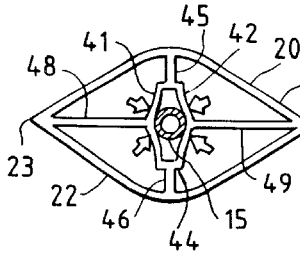
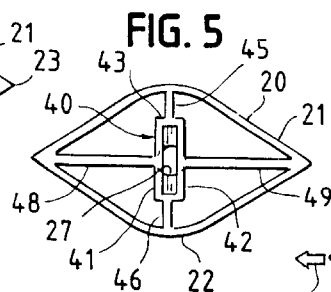
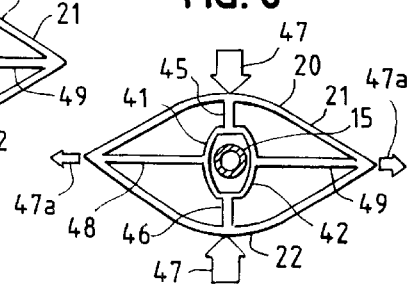

LUBRICATING AND GRIPPING DEVICE FOR URINARY CATHETER PACKAGE

BACKGROUND AND SUMMARY OF THE INVENTION

Urinary catheters for draining the bladder through the urethra are commonly packaged in sterile and pre-lubricated condition in flexible containers or pouches. In some cases, the catheters are intended to be fully removed from such containers at the time of catheterization, whereas in others the containers and catheters may remain in communication with the containers then serving as urine-collecting pouches. Reference may be had to U.S. Pat. Nos. 3,854,483 (Powers), 5,226,530 (Golden), 3,934,721 (Juster et al), 6,004,305 (Hursman et al), 5,147,341 (Starke et al) and 6,053,905 (Daignault et al) as illustrative of the art.

Catheterization commonly involves inserting the distal tip of a catheter (sometimes protected against contamination by an introducer sleeve as disclosed, for example, in U.S. Pat. No. 3,854,483 and U.S. Pat. No. 4,652,259) into the urethra and then longitudinally collapsing and extending the pouch in an accordion-like manner until the tip reaches the bladder. Such action is illustrated, for example, in U.S. Pat. No. 4,062,363 (Bonner). By gripping the remote (proximal) end of the catheter between the walls of the pouch during the pouch-collapsing phase, the catheter is advanced in a distal direction and, conversely, during the pouch-extending phase, the catheter is held against reverse sliding movement by gripping it between the pouch walls near the pouch's distal end. The operation is a two-handed one requiring considerable dexterity to insure that the catheter is advanced during the pouch-collapsing phase and not retracted during the pouch-extending phase.

Complications may arise that make such a procedure even more difficult. For example, fluid pressure may tend to expel the catheter and require the user to continue gripping the catheter between the walls of the pouch to hold it in place during voiding. Because the catheter is lubricated, immobilizing it by applying a gripping force to the walls of the pouch may require more strength and dexterity than patients can provide, thereby precluding self-catheterization.

In an effort to reduce such problems, some packages for prelubricated catheters contain gripping devices that may be squeezed to help hold a catheter against reverse sliding movement (see U.S. Pat. Nos. 6,053,905, 6,004,305 and WO 98/06642). Typically, such gripping devices are designed to engage the side surfaces of a catheter but, since those surfaces are already lubricated, slippage may still readily occur.

Lubricating and gripping systems used in current catheter packages often have other shortcomings as well. Lubricant gel may not be retained in one area of such a package but may be free to migrate into the urine-collective chamber, causing the walls of the pouch to stick together and make voiding more difficult. Squeezable gripping devices, even if properly fitted onto the tip of a catheter during production, may slip off during storage and transport, requiring a user to refit such a device prior to catheterization. Further, in some constructions, lubricant tends to be unevenly distributed over the surfaces of a catheter, causing patient discomfort and risking possible injury during catheterization.

This invention therefore concerns an improved self-lubricating catheter package that overcomes or at least greatly reduces the aforementioned defects and disadvantages of current products. More specifically, this invention involves a catheter package in which lubricant (preferably in the form of a gel) is retained in a housing located within the distal end portion of a pouch. Means are provided to insure even distribution of the lubricant over the surfaces of a catheter during a catheterization procedure. The housing includes gripping means which, in contrast to conventional devices, normally holds a catheter against sliding movement and releases that catheter for movement only when squeezing forces are applied by a user's fingers. Since the gripping means automatically restrains sliding movement of the catheter in the absence of such squeezing forces, the device holds the catheter in place during storage and transport, thereby eliminating the possibility that a user might have to reinsert the catheter into the gripping device prior to use. Further, the gripping device easily holds the catheter in place in the urethra during voiding and also eliminates or greatly reduces the possibility of reverse movement of the catheter during the pouch-collapsing and pouch-extending phases of catheterization. The catheter gripping and lubricating device is therefore believed to be considerably more effective in operation and ease of use than existing devices and, when used in combination with a flexible container or pouch, results in a catheter package that is superior to current assemblies.

Briefly, the catheter gripping and lubricating device includes a deformable and shape-recoverable housing of elastomeric material defining a lubricant chamber. At its distal end, the chamber is substantially closed by an end cap having an axial catheter-receiving passage extending therethrough. The opposite or proximal end of the chamber includes a retention wall that restrains lubricant flow in a proximal direction from the housing. The retention wall is apertured to allow sliding movement of a catheter into and through the lubricant chamber of the housing.

Catheter gripping means is located at the proximal end portion of the housing in advance of (i.e., proximal to) the apertured retention wall and lubricant chamber. The gripping means normally grips opposite side surfaces of a catheter to restrain its sliding movement but is deformable upon the application of squeezing force (by a user's fingers applied against the opposite side walls of the housing) to selectively release the catheter for sliding movement. The catheter gripping means includes a pair of deformable clamping members that normally frictionally engage opposite side surfaces of the catheter, such clamping members extending between and being connected to upper and lower walls of the housing so that squeezing forces applied to those walls will cause the clamping members to bow outwardly away from each other and release the catheter for sliding movement.

The catheter gripping and lubricating device is located within the distal end of a pouch that maintains the catheter in sterile condition prior to use and may advantageously serve as a urine collection pouch during catheterization. Ideally, side surfaces of the guide housing's end cap are heat sealed or otherwise bonded to inside surfaces of the pouch at its distal end. The end cap includes a tubular extension that projects through and beyond the pouch's distal end, and in one preferred embodiment of the invention such extension carries a soft pliant introducer sleeve designed to protect the catheter tip against contamination by non-sterile urethral surfaces immediately adjacent the urethral opening.

A lubricant, preferably in the form of a lubricant gel, is disposed in the lubricant chamber. The passage of the distal end cap, including the extension of that end cap, is of a diameter sufficiently greater than the outside diameter of the catheter to insure that a thin even coating of lubricant is applied to and remains on the catheter as it is advanced into the urethra. In that connection, it is to be noted that squeezing forces applied to the lubricant housing for purposes of releasing the gripping means also helps to insure that lubricant will be forced into contact with the external surfaces of the catheter as it advances through the lubricant chamber.

Other features, objects and advantages of the invention will become apparent from the drawings and specification.

DRAWINGS

FIG. 1 is a top plan view of a catheter package embodying this invention.

FIG. 2 is a perspective view showing the catheter gripping and lubricating device, with a catheter extending therethrough, in solid lines; for clarity of illustration, the enclosing pouch is depicted in phantom.

FIG. 3 is a longitudinal sectional view of the complete catheter package.

FIG. 4 is an enlarged cross sectional view taken along line 4—4 of FIG. 3.

FIG. 5 is a cross sectional view similar to FIG. 4 but showing the housing in an untensioned state prior to insertion of a catheter.

FIG. 6 is a sectional view similar to FIG. 4 but illustrating deformation of the gripping means by the application of squeezing forces to the housing for purposes of releasing a catheter for sliding movement therethrough.

DETAILED DESCRIPTION OF PREFERRED EMBODIMENTS

Figure 7:
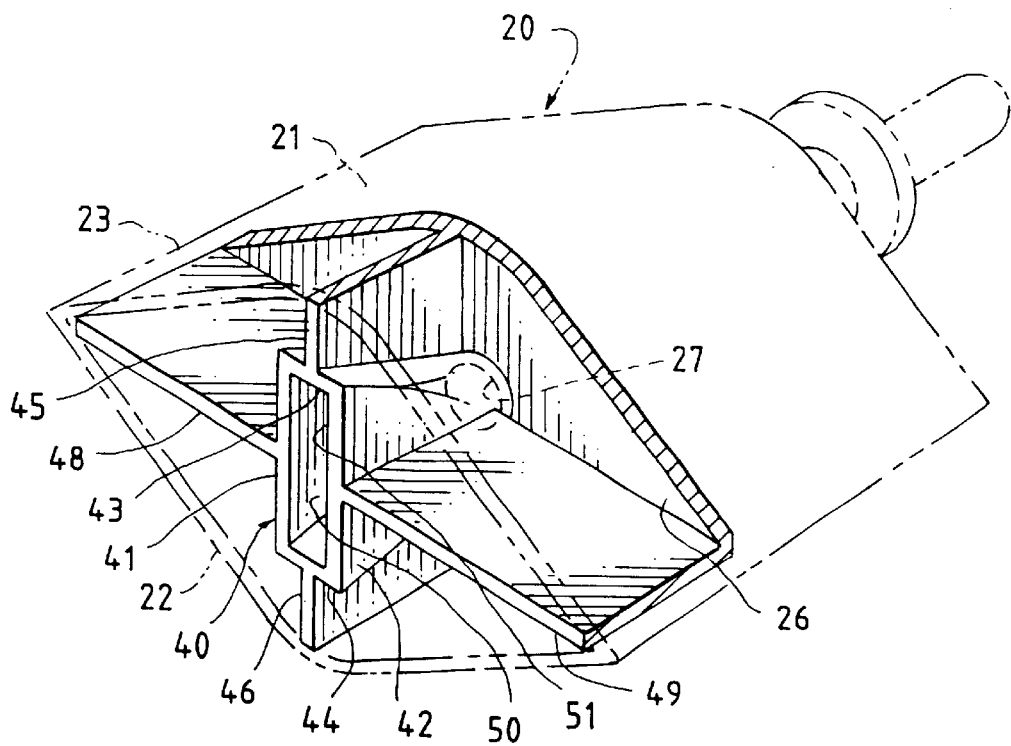
FIG. 7 is a fragmentary perspective view, shown partly in section and partly in phantom, illustrating details of the catheter gripping means.

Referring to the drawings, the numeral 10 generally designates a sterile self-lubricating catheter package comprising a flexible container 11 in the form of a flat, elongate pouch or bag 11 having top and bottom side walls 11a and 11b preferably formed of heat-sealable film. In the illustration given, the pouch is generally rectangular in outline with longitudinal side edges 12, a proximal end 13, and a distal end 14. The pouch may be formed as an extruded tube with proximal end 13 closed by heat seal 13a and distal end 14 sealed by transverse heat seal 14a. The terms "top" and "bottom" are being used here in referring to walls 11a and 11b to facilitate description of the assembly as a whole but, in view of the symmetry of the pouch, it will be understood that these terms are arbitrary and that the pouch may just as easily be placed on a support surface in flipped over condition with 11b constituting the top wall and 11a the bottom wall. Also, while a rectangular configuration is shown, that shape is not considered critical.

Disposed entirely within the pouch is a urinary catheter 15 and a catheter gripping and lubricating device 16. The catheter may take the form of a standard urinary catheter of tubular shape formed of soft flexible thermoplastic material. One or more openings 17 are provided at its distal end. At its proximal end, the catheter may be provided with a frusto-conical fitting 18 which prevents or restrains extraction of the catheter from the pouch through gripping and lubricating device 16 and, if desired, may also be used as a Luer fitting for attachment to a syringe or other suitable instrument or device (after the pouch has been opened at its proximal end). Alternatively, fitting 18 may be omitted and, if desired, some other fitting (which may or may not operate as a stop member) may be provided.

The catheter gripping and lubricating device 16 comprises a tubular guide housing 20 having convexly curved upper and lower side walls 21 and 22 merging along longitudinal edges 23 to define a lubricant chamber 24 of greater width than height. The housing includes cap means 25 sealed to walls 21 and 22 at the distal end of the chamber. Lubricant retention means in the form of a proximal wall portion 26 substantially closes off the proximal end of the chamber 24. The proximal end wall portion 26 has a central aperture 27 for slidably receiving catheter tube 15, and distal end cap 25 has a coaxial passage 28 into which the tip of the catheter extends.

As shown in FIG. 3, end cap 25 also has a distal extension 25a through which passage 28 continues. Extension 25a is disposed externally of pouch 11, projecting a short distance beyond the pouch's distal end 14. The heat seal 14a that joins the walls of the bag together at the pouch's distal end also joins those walls to the upper and lower surfaces of end cap 25.

Distal extension 25a, passage 28, and the tip of sterile catheter 15 may all be protected against contamination by a removable cap (not shown) covering the extension. Alternatively (or additionally), the catheter package 10 thus described may be sealed within a second pouch or bag (not shown) to maintain the package in sterile condition. In the particular embodiment illustrated in the drawings, a soft elastomeric introducer 30 having a tubular sleeve portion 31 and flange 32 is secured to extension 25. The distal end of the sleeve portion 31 is rounded and closed except for one or more slits 33. As shown in FIG. 3, the lumen 34 of the introducer's sleeve portion 31 registers directly with passage 28 of the end cap 25 and its extension 25a. The length of the sleeve portion is such that, upon insertion into the urethra, it will shield the catheter 15 against contact with and contamination by a short stretch of the urethra adjacent the labia.

Use of the introducer 30 is optional. Where provided, its surfaces should be maintained in sterile condition prior to use. Such sterility may be achieved by means of a cap (not shown) removably fitted upon sleeve portion 31, or by locating the entire assembly shown in FIG. 3 within a sterile outer wrap (not shown), or both.

The guide housing 20 is deformable and shape-recoverable, being formed an elastomeric material such as silicone rubber or other polymer having similar properties. At its proximal end, located beyond (in a direction proximally to) the apertured wall 26, is a catheter gripping mechanism 40 formed integrally with the housing. The gripping mechanism includes a pair of laterally-spaced clamping members 41 and 42 extending along opposite sides of catheter 15 and normally engaging the catheter with sufficient force to restrain its longitudinal sliding movement through the housing (FIG. 4). The clamping members are connected to each other along their upper and lower limits by upper and lower connecting walls 43 and 44 which slope radially inwardly in a distal direction (FIGS. 3, 7 and 8) and which in turn are joined to upper and lower walls 21 and 22 by vertical walls 45 and 46 extending along the guide housing's vertical midplane. Since clamping members 41 and 42 are spaced laterally outwardly from that midplane, squeezing forces applied by the fingers to upper and lower walls 21 and 22, in the directions of arrows 47 in FIG. 6, cause the clamping members to bow outwardly and release catheter 15. Such action is aided by horizontal connecting walls 48 and 49 which join each of the clamping members to the walls of the housing adjacent longitudinal edges 23. Since the longitudinal edges are urged apart when squeezing forces are applied in the directions of arrows 47, a pulling action (represented by arrows 47a) also takes place to draw the clamping members outwardly into their catheter-releasing positions.

Figure 8:
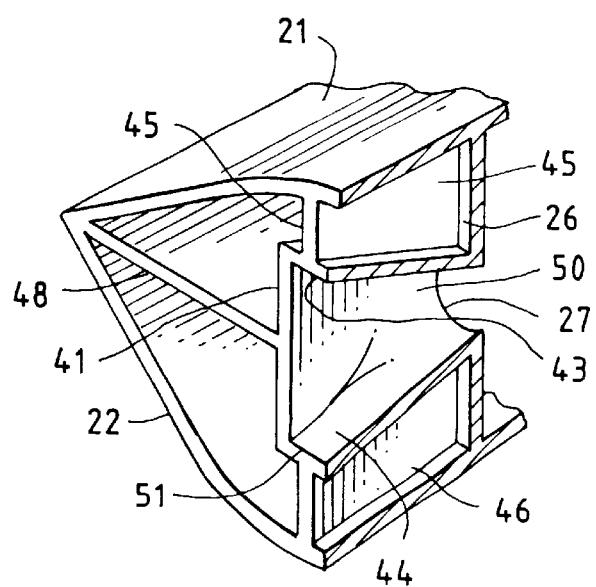
FIG. 8 is a fragmentary perspective view of the distal end of the housing with the catheter gripping means sectioned along its longitudinal vertical mid-plane to further illustrate structural details of the catheter gripping means.

FIGS. 5–8 illustrate the reason for the self-clamping action of the catheter gripping means. Members 41 and 42 are shown to be planar when in untensioned condition. The spacing between the untensioned clamping members is substantially less than the outside diameter of catheter 15, as well as less than the diameter of aperture 27. Before insertion of catheter, members 41 and 42 therefore appear as shown in FIGS. 5, 7 and 8, whereas following insertion the clamping members are forced laterally away from each other, as depicted in FIG. 4, and, because of the forces of elastic recovery normally exerted by the housing, such members grip and restrain the catheter against sliding movement.

It will be noted that the passage 50 through the gripping means 40 changes substantially when viewed both longitudinally and transversely. When the clamping means is in an undeformed state as shown in FIG. 7, the passage 50 terminates at its proximal end in a narrow, vertically elongated rectangular opening 51, and, at its opposite distal end, in circular opening or aperture 27 having a slightly smaller diameter than the outside diameter of the catheter to be extended therethrough. Since the horizontal width of the rectangular opening 51 is less than the diameter of aperture 27, the passage viewed in horizontal section becomes slightly wider in a distal direction. However, when viewed in vertical section (FIG. 8), the same passage tapers sharply in a distal direction throughout the transition from rectangular to circular configuration.

Vertical walls 45 and 46, and horizontal walls 48 and 49 all contribute in causing clamping members 41 and 42 to bow outwardly as squeezing forces are applied in the directions shown by arrows 47 in FIG. 6. In addition, horizontal walls 48 and 49 act to brace the clamping members 41 and 42 and help to ensure a secure gripping force is applied to the sides of a catheter until such time as the housing is deformed by squeezing force as representative in FIG. 6.

A lubricant 52 is located within chamber 24 of housing 20. The lubricant is a liquid or gel and may be any of a variety of materials commonly used for lubricating urinary catheters. Its viscosity may be varied from that of a readily flowable oil to that of a more viscous semi-liquid, although a lubricant gel is generally preferred. Such a lubricant is preferably, but not necessarily, water soluble.

As already indicated, the gripping and lubricating device 16 and catheter 15 would be made available to a user in a protective pouch or envelope 11. Catheter 15 extends through lubricant-containing chamber 24 with its tip located in passage 28 of distal end cap 25. At the time of catheterization, a user squeezes the side walls 21 and 22 together to release the catheter for sliding movement as illustrated in FIG. 6 and then, with the fingers of the other hand, grips the proximal end portion of the catheter between walls 11a and 11b of the pouch and urges the catheter distally. Such action causes the pouch walls to collapse, producing accordion-like folds, as the pouch's proximal end approaches guide housing 20. The user then relieves the squeezing force applied to the guide housing 20, allowing the housing to return to its clamping condition depicted in FIG. 4, and draws the proximal end of the pouch outwardly into its original unfolded condition. The process is repeated until the tip of the catheter has passed through the urethra and reaches the bladder. If the pouch is to be used as a fluid collection device (as shown) urine flows through the catheter into the chamber of the pouch. During a voiding procedure, no squeezing force is applied to guide housing 20, with the result that the guide housing automatically restrains retrograde sliding movement caused by fluid flow and pressure.

The flowable lubricant 52 contained in chamber 24 is applied to the external surfaces of catheter 15 as that catheter is advanced during a catheterization procedure. It is to be noted that the same squeezing force applied to release the gripping action of members 41 and 42 (FIG. 6) also forces the lubricant in chamber 24 into more complete contact with the outer surfaces of the catheter as it is advanced. As shown in FIG. 3, passage 28 through end cap 25 and its extension 25a is of sufficiently larger diameter than the outside diameter of the catheter to insure that a thin uniform coating of lubricant will remain on the catheter as it enters a patient's urethra.

Unlike gripping means sometimes found in other catheter packages, the gripping members 41 and 42 disclosed herein are normally in their catheter-restraining mode and are shifted into releasing positions only when squeezing forces are applied. Effective gripping action is assured because contact is made with unlubricated catheter surfaces, that is, gripping frictional contact occurs with such surfaces well before they reach the lubricant-containing chamber.

Clamping members 41 and 42 have been shown and described as being vertically oriented and extending in directions normal to the plane of the generally flat pouch, and such orientation is indeed preferred. However, it is to be noted that alternatively housing 20 might be rotated 90° relative to the plane of the pouch so that clamping members 41 and 42 are generally parallel with that plane and, in such a case, the catheter gripping mechanism would still be operative although such operation would be somewht less convenient for a user than the operation of the preferred version illustrated.

While in the foregoing, we have disclosed embodiments of the invention in considerable detail for purposes of illustration, it will be understood by those skilled in the art that many of these details may be varied without departing from the spirit and scope of the invention.

What is claimed is:

1. A catheter gripping and lubricating device comprising a deformable and shape-recoverable guide housing of elastomeric material having proximal and distal end portions and defining a lubricant chamber therebetween; an end cap at said distal end portion; lubricant retention means at said proximal end portion for retaining lubricant within said chamber; said end cap having a central passage and said lubricant retention means having a coaxial aperture for sliding movement of a catheter therethrough as such catheter is advanced through said lubricant chamber of said housing; and catheter gripping means in said proximal end portion of said housing for normally and automatically frictionally engaging opposite side surfaces of the catheter to restrain sliding movement thereof but being movable into catheter releasing positions only when said proximal end portion of said housing is squeezed by a user's fingers to permit sliding movement of the catheter through said housing; said gripping means including clamping members with opposing surfaces normally spaced closely together but capable of spreading apart into the catheter releasing positions.

2. The device of claim 1 in which said catheter gripping means is located proximally in relation to said lubricant chamber and said lubricant retention means.

3. A catheter package comprising a catheter gripping and lubricating device comprising a deformable and shape-recoverable guide housing of elastomeric material having proximal and distal end portions and defining a lubricant chamber therebetween; an end cap at said distal end portion; lubricant retention means at said proximal end portion for retaining lubricant within said chamber; said end cap having a central passage and said lubricant retention means having a coaxial aperture for sliding movement of a catheter therethrough as the catheter is advanced through said lubricant chamber of said housing; catheter gripping means in said proximal end portion of said housing for normally and automatically frictionally engaging opposite side surfaces of the catheter to restrain sliding movement thereof but being movable into catheter releasing positions only when said proximal end portion of said housing is squeezed by a user's fingers to permit sliding movement of the catheter through said housing; said gripping means including clamping members with opposing surfaces normally spaced closely together but capable of spreading apart into the catheter releasing positions; and a flowable lubricant disposed in said chamber; and a urinary catheter extending into said chamber through said aperture of said lubricant retention means.

4. The catheter package of claim 3 in which said catheter has a distal tip portion extending into said central passsage of said end cap.

5. The catheter package of claim 3 further comprising a generally flat pouch of flexible thermoplastic film; said pouch having proximal and distal ends and said distal end portion of said housing being sealed to said pouch between walls thereof at the distal end of said pouch.

6. The catheter package of claim 5 in which said end cap includes a tubular extension projecting through and beyond said pouch at the distal end thereof.

7. The catheter package of claim 5 or 6 wherein said passage of said end cap is larger in diameter than an outside diameter of said catheter, whereby, lubricant applied to said catheter when the catheter is advanced through said lubricant chamber remains as a lubricant coating on said catheter as said catheter passes through said passage.

8. The catheter package of claim 6 wherein a tubular introducer is mounted on said extension externally of said pouch, said introducer having a distal end wall provided with at least one self-closing slit capable of opening to allow said catheter to be advanced therethrough, said tubular introducer having a longitudinal dimension sufficient to protect said catheter against contamination by organisms located in a patient's urethra immediately adjacent the labia thereof.

9. A urinary catheter package comprising a catheter gripping and lubricating device comprising a deformable and shape-recoverable guide housing having a generally elliptical cross sectional shape defined by convexly curved opposite side walls merging along longitudinally-extending edges to define a lubricant chamber; said housing having proximal and distal end portions at opposite ends of said chamber; an end cap at said distal end portion; lubricant retention means at said proximal end portion for retaining lubricant within said chamber; said end cap having a axial passage and said lubricant retention means having an aperture coaxial therewith for slidably receiving a urinary catheter therethrough; a urinary catheter extending into said chamber through said aperture of said lubricant retention means; a flowable lubricant within said chamber; and catheter gripping means in said proximal end portion of said housing for normally and automatically gripping said catheter to restrain sliding movement thereof but being deformable upon application of squeezing force by a user's fingers against the curved side walls of said housing to release said catheter for sliding movement therethrough.

10. The catheter package of claim 9 wherein said catheter gripping means is located proximal to said lubricant retention means.

11. The catheter package of claim 9 in which said catheter has a distal tip portion; said catheter normally being restrained against sliding movement by said gripping means with the distal tip portion thereof extending beyond said lubricant chamber and into said passage of said end cap.

12. The catheter package of claim 9 further comprising a generally flat pouch having side walls of flexible thermoplastic film and said catheter gripping and lubricating device is located therein.

13. The catheter package of claim 12 in which said pouch has a distal end portion internally sealed to said distal end portion of said housing.

14. The catheter package of claim 13 in which said end cap includes a tubular extension extending through said pouch at the distal end portion thereof.

15. The catheter package of claim 14 in which said passage of said end cap has a diameter larger than an external diameter of said catheter, whereby, lubricant applied to said catheter as the catheter is advanced through said chamber remains as a lubricant coating on said catheter when the catheter is advanced through the passage of said end cap.

16. The catheter package of claim 15 in which a tubular introducer is mounted on said extension externally of said pouch, said introducer being formed of elastomeric material and having a distal end wall provided with at least one self-closing slit capable of opening to allow said catheter to be advanced therethrough.

17. The catheter package of claim 9 in which said catheter gripping means includes a pair of deformable clamping members normally frictionally engaging opposite sides surfaces of said catheter, said clamping members extending between and being connected to said side walls of said housing; whereby, the squeezing forces applied to said housing side walls causes said deformable clamping members to bow outwardly and release said catheter for sliding movement relative to said housing.

18. The catheter package of claim 17 in which said longitudinally-extending edges of said housing are displaced away from each other when said side walls of said housing are squeezed together; said housing including connecting walls joining mid-portions of said deformable clamping members to said housing along said edges to cause said clamping members to bow outwardly and release said catheter for sliding movement when said side walls of said housing are squeezed together.

19. The catheter package of claim 17 in which said clamping members are each generally planar when in untensioned state prior to insertion of the catheter into said housing.

20. The catheter package of claim 9 in which said flowable lubricant is a lubricant gel.

* * * * *

UNITED STATES PATENT AND TRADEMARK OFFICE
CERTIFICATE OF CORRECTION

PATENT NO. : 6,602,244 B2  
DATED : August 5, 2003  
INVENTOR(S) : Kavanagh et al.

It is certified that error appears in the above-identified patent and that said Letters Patent is hereby corrected as shown below:

Column 6,
Line 56, "such" should be -- the --.

Column 8,
Line 6, "force" should be -- forces --.

Signed and Sealed this

Seventeenth Day of February, 2004

JON W. DUDAS
*Acting Director of the United States Patent and Trademark Office*